United States Patent [19]

Abram et al.

[11] Patent Number: 4,497,900

[45] Date of Patent: Feb. 5, 1985

[54] IMMUNOASSAY FOR *NEISSERIA GONORRHOEAE* ANTIGENS

[75] Inventors: Dinah Abram, Highland Park; Alan S. Armstrong, Waukegan; John E. Herrmann, Hawthorn Woods; Chung-Mei Ling, Chicago, all of Ill.

[73] Assignee: Abbott Laboratories, North Chicago, Ill.

[21] Appl. No.: 479,413

[22] Filed: Mar. 28, 1983

Related U.S. Application Data

[63] Continuation-in-part of Ser. No. 367,698, Apr. 12, 1982, abandoned.

[51] Int. Cl.³ .................. G01N 33/54; G01N 33/56
[52] U.S. Cl. .................. 436/511; 436/518; 436/534; 436/804; 436/811; 436/815; 436/823; 436/825; 435/4; 435/7; 435/243; 435/253; 435/259; 435/871
[58] Field of Search ........ 436/510, 511, 518, 528–531, 436/543–547, 811, 823, 824, 825, 815, 826; 435/4, 7, 14, 21, 25, 243, 259, 871, 253

[56] References Cited

U.S. PATENT DOCUMENTS

| | | | |
|---|---|---|---|
| 3,951,748 | 4/1976 | Devlin | 195/103.5 R |
| 3,974,269 | 8/1976 | Maley | 424/1.1 |
| 4,029,756 | 6/1977 | Gaafar | 424/1.1 |
| 4,066,744 | 1/1978 | Price et al. | 424/12 |
| 4,111,752 | 9/1978 | Weetall | 195/103.5 |
| 4,115,543 | 9/1978 | Wallace et al. | 424/8 |
| 4,140,581 | 2/1979 | Weetall | 195/103.5 |
| 4,150,950 | 4/1979 | Takeguchi et al. | 23/230 B |
| 4,166,765 | 9/1979 | Weetall | 435/26 |
| 4,186,182 | 1/1980 | Gaafar et al. | 424/1.1 |
| 4,188,371 | 2/1980 | Weetall | 424/1.1 |
| 4,241,045 | 12/1980 | Gaafar et al. | 424/1.1 |
| 4,273,756 | 6/1981 | Ling et al. | 424/1 |
| 4,292,403 | 9/1981 | Duermeyer | 435/5 |
| 4,332,890 | 6/1982 | Armstrong | 435/7 |
| 4,351,761 | 9/1982 | Gaafar | 260/112 B |
| 4,390,622 | 6/1983 | Cartwright | 435/18 |
| 4,443,431 | 4/1984 | Buchanan et al. | 424/92 |
| 4,446,230 | 5/1984 | Zubrzycki | 435/6 |

OTHER PUBLICATIONS

Young, H. et al., J. Medical Microbiology, vol. 16, pp. 183–192 (1983).
DeKlerk, E. et al., S. African Medical Journal, vol. 64 (12), pp. 451–454 (1983).
Sarafian, S. K. et al., J. Medical Microbiology, vol. 15, pp. 541–550 (1982).
Johnston, K. H., Infection and Immunity, vol. 28 (1), pp. 101–110 (4–1980).
Thornley, M. J. et al., J. Medical Microbiology, vol. 12 (2), pp. 161–175 (1979).
Chairez, R. et al., Proceedings, American Society for Microbiology, p. 286, abstract C141 (3–1981).
Gaafar, H. A., Archives of Andrology, vol. 3, pp. 337–341 (1979).
Sexually Transmitted Diseases, vol. 5, No. 1, "Detection of *Neisseria gonorrhoeae* in Broth Cultures by Immunologic Methods", Lue, et al., pp. 14–16.

*Primary Examiner*—Ben R. Padgett
*Assistant Examiner*—M. Moskowitz
*Attorney, Agent, or Firm*—James L. Wilcox

[57] ABSTRACT

The present disclosure relates to a solid phase immunoassay for the detection of *Neisseria gonorrhoeae* antigens in a clinical specimen, wherein the *Neisseria gonorrhoeae* antigens to be determined are coated or adsorbed on the solid phase.

15 Claims, No Drawings

IMMUNOASSAY FOR *NEISSERIA GONORRHOEAE* ANTIGENS

This application is a continuation-in-part of U.S. application Ser. No. 367,698, filed Apr. 12, 1982, abandoned.

The present invention relates to an immunoassay procedure for the detection of *Neisseria gonorrhoeae* antigen in a clinical specimen. In particular, the present invention relates to a solid phase immunoassay wherein the *Neisseria gonorrhoeae* antigen to be determined are coated or adsorbed on the solid phase.

BACKGROUND OF THE INVENTION

The persistence of gonorrhea, one of the most prevalent bacterial diseases reported in humans, as a major health problem has resulted in the development of numerous methods for detection of *Neisseria gonorrhoeae*.

Currently accepted procedures for the determination of gonococcal infection rely primarily upon culture techniques. Typical culture techniques include procedures described in *Criteria And Techniques For The Diagnosis Of Gonorrhea*, published by the Center for Disease Control, Atlanta, Ga. In such culture procedures, a specimen, i.e., a urethral or cervical sample, is placed on an acceptable culture medium, i.e., Thayer-Martin medium. The cultures are incubated at 37° C. in a 5% carbon dioxide atmosphere for 24 to 48 hours. The culture plates are thereafter inspected for the appearance of *Neisseria gonorrhoeae* colonies. Suspect colonies are gram-stained and tested for oxidase activity. Generally, presumptive diagnosis of gonococcal infection in males is determined by obtaining urethral cultures which exhibit oxidase-positive colonies of gram-negative "coffee-bean" shaped diplococci when cultured on Thayer-Martin medium. In females, gonococcal infection may be diagnosed by examining cervical cultures on Thayer-Martin medium wherein oxidase-positive colonies of gram-negative diplococci appear. Organisms from presumptively identified colonies of *Neisseria gonorrhoeae* are frequently confirmed by sugar fermentation, fluorescent antibody staining or coagglutination. However such culture procedures are laborious, time-consuming and are generally limited to the detection of "living cells". When culture methods are utilized, a specimen may be taken at one location and shipped to a laboratory, usually at another location, where the organisms are cultured and identified. Thus, these culture procedures may require several days before results are obtained. Furthermore, results obtained from culture procedures may be erroneous, if, rather exacting conditions for preservation, shipment, and culturing of the bacteria are not followed.

In addition to culture procedures, various radiolabeled and enzymatic immunoassay procedures for the detection of *Neisseria gonorrhoeae* have been described. However, such procedures, such as disclosed in U.S. Pat. Nos. 4,066,744; 3,974,269; and 3,951,748 involve radio or enzymatic immunoassays wherein antibodies to *Neisseria gonorrhoeae* in blood serum samples are detected as a means of diagnosing gonorrhea. The results obtained from such immunoassays may be inconclusive because such procedures generally lack requisite specificity and sensitivity. False-positive or false-negative results may be obtained when antibodies to *Neisseria gonorrhoeae* rather than antigens are detected because antibodies are produced only in response to an infectious agent, i.e., an antigen, in the body and antibodies often remain long after the disease has been cured. Therefore, in order to accurately diagnose the presence of infection, it is preferred to assay for antigens rather than antibodies. U.S. patent application Ser. No. 905,575 describes a reverse passive hemagglutination assay for *Neisseria gonorrhoeae* antigens. However, this reverse passive hemagglutination assay procedure cannot be employed to directly assay clinical specimens. In accordance with the disclosed reverse passive hemagglutination assay procedure, the clinical sample must initially be cultured, and the culture is then itself assayed. In addition, since the method disclosed requires that a sample be cultured, the method possesses some of the disadvantages inherently associated with culture techniques.

Therefore, it is an object of the present invention to provide a solid phase immunoassay procedure for the detection of *Neisseria gonorrhoeae* antigens having the accuracy of the culture techniques but eliminating the disadvantages associated with the known immunoassay and culture procedures.

SUMMARY OF THE INVENTION

The present invention to an immunoassay for determining *Neisseria gonorrhoeae* antigen in a clinical specimen comprising:

(a) lysing bacterial cells in the specimen to release *Neisseria gonorrhoeae* antigen;

(b) coating a bare solid support with the lysed *Neisseria gonorrhoeae* antigen;

(c) treating the antigen coated solid support with gonococcal antibody to form an antigen-gonococcal antibody complex on the solid support;

(d) treating the antigen-gonococcal antibody complex with antiglobulin; and (e) determining the antiglobulin bound to the antigen-gonococcal antibody complex as a measure of the *Neisseria gonorrhoeae* antigen in the specimen.

DETAILED DESCRIPTION OF THE INVENTION

In accordance with the methods of the present invention, a clinical specimen is obtained from a patient suspected of having gonorrhea utilizing conventional medical and microbiological techniques. Such clinical specimens include, for example, swab specimens obtained from the cervix, urethra, throat or anus of a patient and body fluids such as synovial fluid or fluid from lesions. The clinical specimens thus obtained consists of bacterial cells containing the *Neisseria gonorrhoeae* antigen to be determined. In order to increase the sensitivity of the assay, it is preferred to lyse the bacteria cells to release *Neisseria gonorrhoeae* antigens in the specimen thereby increasing the number of antigenic sites available for binding to gonococcal antibody. Conventional techniques that may be employed to lyse the bacteria to release antigens include for example, the use of solvent dilution or high pH lysing solutions, heating, enzyme treatment, and physical agitation such as sonication and centrifugation. In a preferred embodiment of the present invention, the swab specimen is placed into a suitable lysing medium. Illustrative of suitable lysing media include, for example, phosphate buffered saline, saline and water. It is preferred to employ phosphate buffered saline. The submerged swab is rapidly twisted back and forth for about fifteen seconds or vortexed in order to release *Neisseria gonorrhoeae* antigens into the medium.

It has unexpectedly been found that the addition of a surfactant such as sodium dodecylsulfate, Triton X-100, Tween-80 or sodium deoxycholate to the lysing medium increases the sensitivity of the method of the present invention. It has been found that the addition of deoxycholate salts, preferably sodium deoxycholate, to the lysing medium produces superior sensitivity and specificity with respect to the results obtained employing the method of the present invention.

According to the preferred embodiment of the present invention, the lysing medium containing the *Neisseria gonorrhoeae* antigen to be assayed is contacted with a bare solid support. The term "bare solid support" refers to a solid support that is untreated or uncoated with either proteins or antibody specific for *Neisseria gonorrhoeae* antigen. That is, there is no chemical or immunological binding between the *Neisseria gonorrhoeae* antigen to be determined and any substance that may be found on the solid support. The lysing medium containing the *Neisseria gonorrhoeae* antigen and the solid support is incubated for a sufficient period of time to permit the *Neisseria gonorrhoeae* antigen to "coat" or "absorb" onto the solid support. Following the incubation period, the antigen coated solid support is washed with water or buffer to remove unadsorbed bacteria and tissue debris. The antigen coated solid support is brought in contact with gonococcal antibody. The resulting mixture is incubated for a sufficient period of time to allow formation of antigen-gonococcal antibody complex on the solid support. The complex on the solid support is washed with water or buffer to remove unbound gonococcal antibody and then treated with antiglobulin. The resulting mixture is incubated for a period of time sufficient to allow the formation of an antigen-gonococcal antibody-antiglobulin complex on the solid support. The complex thus formed is washed with water or buffer and the amount of antiglobulin bound to antigen-gonococcal antibody complex is determined as a measure of the *Neisseria gonorrhoeae* antigen in the sample.

The term "solid support" refers to an insoluble polymeric material sorptive for the antigen. Known materials of this type include hydrocarbon polymers such as polystyrene, polypropylene, polybutylene, butyl rubber and other synthetic rubbers. Other suitable organic polymers include silastic derivatives, polymers of acrylates, polymers of methacrylates, and polymers of vinyl chloride such as polyvinylchloride. Copolymers such as graft copolymers of polystyrene are also useful. In addition to the foregoing materials, the solid support surface may comprise silica gel, silicone wafers, glass insoluble protein metals and the solid support may be in the form of beads, tubes, strips, disks, microtitration plates and the like.

The term "gonococcal antibody" refers to an antibody that is "immunoreactive" with one or more strains of *Neisseria gonorrhoeae* antigens, and is raised in a human or nonhuman species such as rabbit, goat, horse, sheep, guinea pig, etc. The gonococcal antibodies effective in the methods of the present invention are produced employing strains of *Neisseria gonorrhoeae* as immunogens in accordance with known techniques. In addition, because various strains of *Neisseria gonorrhoeae* may be present in a particular specimen, it is preferred to employ a "pool" of immunogens from various strains in the serial immunization of an animal. A pool of immunogens is prepared by combining individual strains of *Neisseria gonorrhoeae*. The pool of immunogens is employed for the serial immunization of an animal to yield serums containing antibodies to all of the strains comprising the pool. The serum thus obtained is then employed as the gonococcal antibody in the methods of the present invention.

The term "antiglobulin" refers to an antibody specific for a species for which the gonococcal antibody was derived and is raised in a nonhuman species such as rabbit, goat, horse, sheep, guinea pig, etc. The amount of antiglobulin bound to the antigen-gonococcal antibody complex may be determined as a measure of the *Neisseria gonorrhoeae* antigen in the sample. The antiglobulin may be directly labeled by conventional fluorescent dyes, enzymes or radioactive labels to permit determination of the amount bound, or it may be indirectly labeled by further reaction, for example, with fluorescent dyes, enzymes or radioactive labels by conventional methods.

It is preferred to employ antiglobulin directly labeled with an enzyme. Examples of enzymes include catalase, peroxidase, urease, glucose oxidase, phosphatase, and the like. If direct labeling of the antiglobulin is employed, following the addition of labeled antibody and formation of the labeled complex, an enzyme substrate is added to the liquid and/or solid phase of the reaction mixture and an enzyme determination is performed by conventional colorimetric, fluorometric, or spectrophotometric techniques. In the case of indirect labeling, that is, the antiglobulin is unlabeled, the complex formed upon addition of the unlabeled antiglobulin is washed to remove unbound antiglobulin and is subsequently reacted with a labeled antibody to the antiglobulin and the bound labeled antibody is then measured.

For the purpose of giving those skilled in the art a better understanding of the present invention, the following illustrative, nonlimiting examples are given. The gonococcal antibody employed in the Examples was produced utilizing *Neisseria gonorrhoeae* strains ATCC 31397, 31398, 31399, 31400, 31401, 31402, 31403, 31404, 31405, 31406, and 31407 which are described in greater detail in copending application Ser. No. 905,575, and are on deposit at the American Type Culture Collection, 12301 Parklawn, Rockville, Md.

EXAMPLE I

1. A urogenital swab sample is placed into a tube containing 1 ml of phosphate buffered saline (pH 7.2) with 0.1% sodium deoxycholate and 1:10,000 thimerosal. After five minutes, the submerged swab is rapidly twisted back and forth for about fifteen seconds or vortexed thereby releasing *Neisseria gonorhoeae* antigen into the buffered solution. The swab is then rotated against the inner edge of the tube.

2. A 200 µl aliquot of the buffered solution containing the *Neisseria gonorrhoeae* antigen is added to appropriate wells of the reaction tray containing a plastic bead and is covered and incubated at 37° C. for fifteen minutes.

3. The plastic bead is washed with water to remove unadsorbed bacteria and tissue debris.

4. To the wells containing the washed beads is added 200 µl of a solution containing 10 µg/ml of rabbit gonococcal antibody in 100% normal human serum containing 0.1% Tween-20, 0.005M ethylenediaminetetraacetic acid and 1:10,000 thimerosal.

5. The reaction trays are covered and incubated for about fifteen minutes at 37° C.

6. Following this second incubation, unbound gonococcal antibody is removed from the wells and the beads are washed with water.

7. To the wells containing the washed beads is added 200 μl of a solution containing 1 μg/ml of antibody to rabbit IgG covalently linked to horseradish peroxidase, 45% fetal calf serum, 0.15% Tween-20, 5% normal human serum, 0.005M ethylenediaminetetraacetic acid and 1:10,000 thimerosal, in 0.05M Tris buffer (pH 7.2).

8. The reaction trays are covered and incubated for about fifteen minutes at 37° C.

9. Following the incubation, unbound antibody to rabbit IgG-horseradish peroxidase is removed and the beads are washed with water.

10. The beads are transferred to assay tubes to which is added 300 μl of a freshly prepared substrate solution containing approximately 27 mg of o-phenylenediamine 2HCl in 5 ml of citrate-phosphate buffer (pH 5.5) containing 0.02% hydrogen peroxide and 0.01% thimerosal. The tubes are incubated for ten minutes at room temperature.

11. Following the incubation, 1 ml of 1N hydrochloride acid was added to each tube.

12. The appearance of a yellow color in the tube, qualitatively indicates the presence of *Neisseria gonorrhoeae* antigens in the sample.

13. The absorbance of the resulting solutions are measured at 492 nm using a spectrophotometer. The intensity of color is proportional to the number of *Neisseria gonorrhoeae* antigen present in the sample.

EXAMPLE II

A strain of *Neisseria gonorrhoeae*, originally isolated from a patient having gonorrhea, is grown on Thayer-Martin agar in a candle extinction jar. After overnight incubation at 37° C., the bacteria are removed from the agar surface with a cotton swab. A suspension of *Neisseria gonorrhoeae* is made in phosphate-buffered saline 0.01M, pH 7.15, and adjusted to an optical density of 0.52 at 630 nm. This concentration is approximately equal to $10^8$ viable organisms per milliliter. Dilutions of the concentrated suspension are prepared in phosphate-buffered saline containing 0.1% sodium deoxycholate and are analyzed in accordance with the procedures described in Example I.

The results in Table I illustrate that approximately 200 organisms/200 μL are detected. A positive test for *Neisseria gonorrhoeae* antigens in Tables I–IV is indicated by an absorbance ($A_{492}$) greater than or equal to 0.150 plus the value of the background (negative control).

TABLE I

| | Sensitivity For Detection Of *Neisseria gonorrhoeae* | |
|---|---|---|
| $CFU^a$/200 μL In The Sample | $A_{492}^b$ | Detection Of *Neisseria gonorrhoeae* Antigens |
| 2000 | 1.251 | Positive |
| 1000 | 0.626 | Positive |
| 500 | 0.269 | Positive |
| 200 | 0.199 | Positive |

TABLE I-continued

| | Sensitivity For Detection Of *Neisseria gonorrhoeae* | |
|---|---|---|
| $CFU^a$/200 μL In The Sample | $A_{492}^b$ | Detection Of *Neisseria gonorrhoeae* Antigens |
| 100 | 0.087 | Negative |
| 20 | 0.053 | Negative |
| Negative Control | 0.034 | — |

$^a$Colony Forming Units
$^b A_{492} \geq 0.184$ is positive

EXAMPLE III

To illustrate the specificity of the method of the present invention, various organisms which may be commonly found in the urogenital area, are analyzed to determine reactivity with respect to the described method.

Organisms are grown on appropriate conventional culture media. Suspensions are prepared and diluted as described in Example II. The *Neisseria gonorrhoeae* control is diluted 1:10,000 to produce a sample containing approximately $10^4$ viable units/ml and the suspension containing the organisms to be assayed are diluted 1:10 to produce a sample containing approximately $10^7$ viable units/ml. The diluted samples are analyzed in accordance with the methods described in Example I. Many of the organisms tested included organisms of the type associated with a specimen (i.e., cervical swab) commonly used to test for Neisseria especially, *Neisseria gonorrhoeae*. The results are summarized in Table II.

TABLE II

| Specificity With Respect To Heterologous Bacteria | | |
|---|---|---|
| Microorganism | $A_{492}^c$ | Detection Of *Neisseria gonorrhoeae* Antigens |
| *Escherichia coli* | 0.089 | Negative |
| *Candida albicans* | 0.070 | Negative |
| *Acinetobacter calcoaceticus* | 0.090 | Negative |
| *Klebsiella pneumoniae* | 0.096 | Negative |
| *Proteus vulgaris* | 0.114 | Negative |
| *Streptococcus faecalis* | 0.095 | Negative |
| *Lactobacillus plantarium* | 0.110 | Negative |
| *Corynebacterium hofmannii* | 0.169 | Negative |
| *Staphylcoccus epidermidis* | 0.115 | Negative |
| *Neisseria gonorrhoeae* (control) | 1.274 | Positive |
| Negative control | 0.069 | — |

$^c A_{492} \geq 0.219$ is positive

EXAMPLE IV

A total of 313 urethral swabs from males and 324 endocervical swabs from females were collected at local venereal disease clinics. Soon after the swab was collected, a sample was assayed by the standard culture procedure using Thayer-Martin selective agar. The samples were also assayed in accordance with the procedures described in Example I.

The results are represented in Table III.

TABLE III

| Group | Number | Results Obtained From Culture Procedure[d] | Detection of Neisseria Gonorrhoeae Antigens Pos. | Neg. | % Sensitivity | % Specificity | % Agreement With Culture |
|---|---|---|---|---|---|---|---|
| Male | 121 | Positive | 120 | 1 | 99.2 (120/121) | — | 98.4 (308/313) |
| Male | 192 | Negative | 4 | 188 | — | 97.9 (188/192) | |
| Female | 66 | Positive | 59 | 7 | 89.4 (59/66) | — | 94.4 (306/324) |
| Female | 258 | Negative | 11 | 247 | — | 95.7 (247/258) | |
| Totals | | | | | | | |
| Male & | 187 | Positive | 179 | 8 | 95.7 (179/187) | — | 96.4 (614/637) |
| Female | 450 | Negative | 15 | 435 | — | 96.7 (435/450) | |

[d]A culture is considered positive only if it is confirmed by sugar fermentation tests.
[e]Results obtained using the procedure described in Example I Another embodiment of the present invention relates to the use of a labeled gonococcal antibody in lieu of the previously described gonococcal antibody and antiglobulin. A "labeled gonococcal antibody" refers to a gonococcal antibody that is directly labeled by conventional fluorescent dyes, enzymes or radioactive labels. If a labeled gonococcal antibody is utilized, it is preferred to employ gonococcal antibody directly labeled with an enzyme. Examples of enzymes include catalase, peroxidase, urease, glucose oxidase, phosphatase, and the like. A labeled gonococcal antibody may be utilized in the methods of the present invention in accordance with the following procedure. The medium containing the *Neisseria gonorrhoeae* antigen to be assayed is contacted with a solid support and is incubated for a sufficient period of time to permit an effective amount of the antigen to coat onto the solid support. Following the incubation period, the antigen coated solid support is washed with water or buffer to remove unadsorbed bacteria and tissue debris. The antigen coated solid support is brought in contact with labeled gonococcal antibody. The resulting mixture is incubated for a sufficient period of time to allow formation of antigen-labeled gonococcal antibody complex on the solid support. The antigen-labeled gonococcal antibody complex on the solid support is washed with water or buffer to remove unbound labeled gonococcal antibody. The amount of labeled gonococcal antibody bound to the antigen complex is determined as a measure of the *Neisseria gonorrhoeae* antigen in the sample.

The following examples illustrate the use of labeled gonococcal antibody in the methods of the present invention.

EXAMPLE V

1. A urogenital swab sample is placed into a tube containing 1 ml of phosphate buffered saline (pH 7.2) with 0.1% sodium deoxycholate and 1:10,000 thimerosal. After five minutes, the submerged swab is rapidly twisted back and forth for about fifteen seconds or vortexed thereby releasing *Neisseria gonorrhoeae* antigens into the buffered solution. The swab is then rotated against the inner edge of the tube.

2. A 200 μl aliquot of the buffered solution containing the sample is added to appropriate wells of the reaction tray containing a plastic bead and is covered and incubated at 37° C. for fifteen minutes.

3. The plastic bead is washed with water to remove unadsorbed bacteria and tissue debris.

4. To the wells containing the washed beads is added 200 μl of a solution containing 10 μg/ml of a mixture of rabbit gonococcal antibody covalently linked to horseradish peroxidase in 100% normal human serum, to which 0.1% Tween-20, 0.005M ethylenediaminetetraacetic acid and 1:10,000 thimerosal.

5. The reaction trays are covered and incubated for about fifteen minutes at 37° C.

6. Following the incubation, unbound gonococcal antibody-horseradish peroxidase is removed and the beads are washed with water.

7. The beads are transferred to assay tubes to which is added 300 μl of a freshly prepared substrate solution containing approximately 27 mg of o-phenylenediamine 2HCl in 5 ml of citrate-phosphate buffer (pH 5.5) containing 0.02% hydrogen peroxide and 0.01% thimerosal. The tubes are incubated for ten minutes at room temperature.

8. Following the incubation, 1 ml of 1N hydrochloric acid was added to each tube.

9. The appearance of the yellow color in the tube, qualitatively indicates the presence of *Neisseria gonorrhoeae* antigen in the sample.

10. The absorbance of the resulting solutions are measured at 492 nm using a spectrophotometer. The intensity of color is proportional to the number of *Neisseria gonorrhoeae* antigens present in the sample.

EXAMPLE VI

A laboratory strain of *Neisseria gonorrhoeae*, originally isolated from a patient having gonorrhea, is grown on Thayer-Martin agar in a candle extinction jar. After overnight incubation of 37° C., the bacteria are removed from the agar surface with a cotton swab. A suspension of *Neisseria gonorrhoeae* bacteria is made in phosphate-buffered saline 0.01M, pH 7.15, and adjusted to an optical density of 0.52 at 630 nm. This concentration is approximately equal to $10^8$ viable organisms per milliliter. Dilutions of the concentrated suspension are prepared in phosphate buffered saline containing 0.1% sodium deoxycholate and were analyzed in accordance with the procedure described in Example V.

The results in Table IV illustrate that approximately 10,000 organisms/200 μL are detected.

TABLE IV

| CFU[f]/200 μL In The Sample | $A_{492}$[g] | Detection Of Neisseria gonorrhoeae Antigens |
|---|---|---|
| $2 \times 10^5$ | 2.026 | Positive |
| $2 \times 10^4$ | 0.785 | Positive |
| $10^4$ | 0.613 | Positive |
| $2 \times 10^3$ | 0.549 | Negative |
| $10^3$ | 0.458 | Negative |
| 200 | 0.495 | Negative |
| 100 | 0.452 | Negative |
| 20 | 0.440 | Negative |

TABLE IV-continued

| CFU$^f$/200 μL In The Sample | A$_{492}$$^g$ | Detection Of Neisseria gonorrhoeae Antigens |
|---|---|---|
| Negative Control | 0.440 | — |

$^f$Colony Forming Units
$^g$A$_{492}$ ≧ 0.590 is positive

As evidenced by the above examples, the methods of the present invention provide a solid phase immunoassay for *Neisseria gonorrhoeae* antigen having the sensitivity and specificity of conventional culture techniques. The method of the present invention minimizes sample handling and possesses the ability to detect both live and dead organisms. In addition, qualitative as well as quantitative results may be obtained.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A method for determining *Neisseria gonorrhoeae* antigen in a clinical specimen comprising:
   (a) lysing *Neisseria gonorrhoeae* cells in the specimen to release *Neisseria gonorrhoeae* antigen;
   (b) coating a bare solid support with the *Neisseria gonorrhoeae* antigen;
   (c) separating the antigen coated solid support from the specimen;
   (d) treating the antigen coated solid support with gonococcal antibody to form antigen-gonococcal antibody complex on the solid support;
   (e) separating the antigen-gonococcal antibody complex from unbound gonococcal antibody;
   (f) treating the antigen-gonococcal antibody complex with labeled antiglobulin, to form an antigen-gonococcal antibody-labeled antiglobulin complex on the solid support;
   (g) separating the antigen-gonococcal antibody-labeled antiglobulin complex from unbound labeled antiglobulin; and
   (h) determining the labeled antiglobulin bound to the antigen-gonococcal antibody complex as a measure of the *Neisseria gonorrhoeae* antigen in the specimen.

2. A method according to claim 1 wherein the *Neisseria gonorrhoeae* cells are lysed using a buffered saline solution and a surfactant.

3. A method according to claim 2 wherein the surfactant is a deoxycholate salt.

4. A method according to claim 3 wherein the deoxycholate salt is sodium deoxycholate.

5. A method according to claim 1 wherein the gonococcal antibody is produced by immunizing an animal with a pool of *Neisseria gonorrhoeae* strains.

6. A method according to claim 1 wherein the antiglobulin is labeled with an enzyme.

7. A method according to claim 1 wherein the separation steps are performed by aspiration and washing with water.

8. A method for determining *Neisseria gonorrhoeae* antigen in a clinical specimen comprising:
   (a) lysing *Neisseria gonorrhoeae* cells in the specimen to release *Neisseria gonorrhoeae* antigen;
   (b) coating a bare solid support with the *Neisseria gonorrhoeae* antigen;
   (c) separating the antigen coated solid support from the specimen;
   (d) treating the antigen coated solid support with gonococcal antibody to form an antigen-gonococcal antibody complex on the solid support;
   (e) separating the antigen-gonococcal antibody complex from unbound gonococcal antibody;
   (f) treating the antigen-gonococcal antibody complex with antiglobulin, to form an antigen-gonococcal antibody-antiglobulin complex on the solid support;
   (g) separating the antigen-gonococcal antibody-antiglobulin complex from unbound antiglobulin;
   (h) treating the antigen-gonococcal antibody-antiglobulin complex with labeled antibody to the antiglobulin to form an antigen-gonococcal antibody-antiglobulin-labeled antibody complex on the solid support;
   (i) separating the antigen-gonococcal antibody-antigloblin-labeled antibody complex from unbound labeled antibody; and
   (j) determining the labeled antibody bound to the antigen-gonococcal antibody-antiglobulin complex as a measure of the *Neisseria gonorrhoeae* antigen in the specimen.

9. A method according to claim 8 wherein the *Neisseria gonorrhoeae* cells are lysed using a buffered saline solution and a surfactant.

10. A method according to claim 9 wherein the surfactant is a deoxycholate salt.

11. A method according to claim 10 wherein the deoxycholate salt is sodium deoxycholate.

12. A method according to claim 8 wherein the gonococcal antibody is produced by immunizing an animal with a pool of *Neisseria gonorrhoeae* strains.

13. A method according to claim 8 wherein the antiglobulin is labeled with an enzyme.

14. A method according to claim 8 wherein the separation steps are performed by aspiration and washing with water.

15. A method for determining *Neisseria gonorrhoeae* antigen in a clinical speciman comprising:
   (a) lysing *Neisseria gonorrhoeae* cells in the specimen to release *Neisseria gonorrhoeae* antigen;
   (b) coating the bare solid support with the *Neisseria gonorrhoeae* antigen;
   (c) separating the antigen coated solid support from the specimen;
   (d) treating the antigen coated solid support with labeled gonococcal antibody;
   (e) separating the antigen coated solid support treated with labeled gonococcal antibody from unbound labeled gonococcal antibody; and
   (f) determining the labeled gonococcal antibody bound to the antigen coated solid support as a measure of the *Neisseria gonorrhoeae* antigen in the specimen.

* * * * *